(12) United States Patent
Ramakrishnan et al.

(10) Patent No.: US 12,312,906 B2
(45) Date of Patent: May 27, 2025

(54) METHODS, APPARATUS AND SYSTEMS FOR CREATING BISMUTH ALLOY PLUGS FOR ABANDONED WELLS

(71) Applicant: Schlumberger Technology Corporation, Sugar Land, TX (US)

(72) Inventors: Terizhandur S. Ramakrishnan, Boxborough, MA (US); Quincy K. Elias, Hyde Park, MA (US); Hua Zhang, Cambridge, MA (US); Youssef Magdy Abdou Mohamed Elkady, Stanford, CA (US); Yixuan Feng, Duluth, GA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 18/456,735

(22) Filed: Aug. 28, 2023

(65) Prior Publication Data
US 2024/0093571 A1    Mar. 21, 2024

Related U.S. Application Data

(63) Continuation of application No. 15/733,723, filed as application No. PCT/US2019/017274 on Feb. 8, (Continued)

(51) Int. Cl.
*E21B 33/13* (2006.01)
*C09K 8/42* (2006.01)
(Continued)

(52) U.S. Cl.
CPC ............. *E21B 33/13* (2013.01); *C09K 8/426* (2013.01); *C09K 8/46* (2013.01); *C22C 12/00* (2013.01);
(Continued)

(58) Field of Classification Search
CPC ........ E21B 33/13; E21B 33/12; E21B 33/138; E21B 33/143; C09K 8/426
See application file for complete search history.

(56) References Cited

U.S. PATENT DOCUMENTS

| | | |
|---|---|---|
| 4,044,834 A | 8/1977 | Perkins |
| 4,898,240 A | 2/1990 | Wittrisch |
| (Continued) | | |

FOREIGN PATENT DOCUMENTS

| | | |
|---|---|---|
| WO | 2017030806 A1 | 2/2017 |
| WO | 2018063829 A1 | 4/2018 |
| WO | 2018191158 A1 | 10/2018 |

OTHER PUBLICATIONS

Abdelal et al., "Numerical simulation of a patent technology for sealing of deep-sea oil wells using nonlinear finite element method", Journal of Petroleum Science and Engineering, vol. 133, pp. 192-200, 2015.
(Continued)

*Primary Examiner* — Catherine Loikith
(74) *Attorney, Agent, or Firm* — Michael L. Flynn; Jeffrey D. Frantz

(57) ABSTRACT

A wellbore is plugged using a bismuth alloy. In one embodiment, the bismuth alloy comprises an alloy of bismuth and tin. In another embodiment, the bismuth alloy comprises an alloy of bismuth and silver. The wellbore can be arranged so that a liquid bismuth alloy sets with an excess pressure of the plug relative to the borehole fluid pressure along a desired seal height distance. Other aspects are described and claimed.

9 Claims, 9 Drawing Sheets

Related U.S. Application Data 2019, now Pat. No. 11,739,609, which is a continuation-in-part of application No. PCT/US2018/034422, filed on May 24, 2018, and a continuation-in-part of application No. PCT/US2018/034418, filed on May 24, 2018.

(60) Provisional application No. 62/652,015, filed on Apr. 3, 2018.

(51) Int. Cl.
| | |
|---|---|
| *C09K 8/46* | (2006.01) |
| *C22C 12/00* | (2006.01) |
| *E21B 29/12* | (2006.01) |
| *E21B 33/12* | (2006.01) |
| *E21B 33/134* | (2006.01) |
| *E21B 33/138* | (2006.01) |
| *E21B 33/14* | (2006.01) |
| *G01N 33/2028* | (2019.01) |

(52) U.S. Cl.
CPC .............. *E21B 29/12* (2013.01); *E21B 33/12* (2013.01); *E21B 33/1208* (2013.01); *E21B 33/134* (2013.01); *E21B 33/138* (2013.01); *E21B 33/143* (2013.01); *G01N 33/2028* (2019.01)

(56) References Cited

U.S. PATENT DOCUMENTS

| | | | |
|---|---|---|---|
| 5,667,010 | A | 9/1997 | Boyd et al. |
| 5,791,417 | A | 8/1998 | Haugen et al. |
| 5,832,409 | A | 11/1998 | Ramakrishnan et al. |
| 6,474,414 | B1 | 11/2002 | Gonzalez et al. |
| 7,152,657 | B2 | 12/2006 | Bosma et al. |
| 7,640,965 | B2 | 1/2010 | Bosma et al. |
| 8,627,901 | B1 | 1/2014 | Underwood et al. |
| 8,701,794 | B2 | 4/2014 | Zediker et al. |
| 9,359,848 | B2 | 6/2016 | Surjaatmadja et al. |
| 11,401,777 | B2 | 8/2022 | Shafer |
| 11,741,275 | B2 * | 8/2023 | Singh ..................... E21B 47/07 166/250.01 |
| 2004/0040710 | A1 | 3/2004 | Eden et al. |
| 2004/0149418 | A1 | 8/2004 | Bosma et al. |
| 2006/0144591 | A1 | 7/2006 | Gonzalez et al. |
| 2010/0155085 | A1 | 6/2010 | Spencer |
| 2010/0258309 | A1 | 10/2010 | Ayodele et al. |
| 2012/0298359 | A1 | 11/2012 | Eden |
| 2013/0087335 | A1 | 4/2013 | Carragher et al. |
| 2014/0352964 | A1 | 12/2014 | Surjaatmadja et al. |
| 2016/0145962 | A1 | 5/2016 | Carragher |
| 2017/0247971 | A1 | 8/2017 | Rivas Diaz |
| 2018/0003001 | A1 | 1/2018 | Pipchuk et al. |
| 2018/0066489 | A1 | 3/2018 | Pipchuk et al. |
| 2021/0148190 | A1 | 5/2021 | Ramakrishnan et al. |
| 2021/0155841 | A1 | 5/2021 | Ramakrishnan et al. |
| 2021/0164322 | A1 | 6/2021 | Ramakrishnan et al. |

OTHER PUBLICATIONS

Search Report and Written Opinion of International Patent Application No. PCT/US2018/034422 issued on Oct. 2, 2018; 16 pages.
Yili, "An Optimal Design for Millimeter-Wide Facture Plugging Zone", Natural Gas Industry B., vol. 2(1), Jan. 2015, pp. 113-119.
Search Report and Written Opinion of International Patent Application No. PCT/US2018/034418 issued on Sep. 28, 2018; 18 pages.
Single Shear Test from Effect of Blade Thickness on Shear Strength, Appendix A, Department of Defense, 1973. MIL-STD-1312, Test No. 20, 28 pages.
Ramakrishnan et al., "Measurement of ultralow permeability", AIChE Journal, 62(4):1278{1293, 2016.
Search Report and Written Opinion of International Patent Application No. PCT/US2019/017274 issued on Jun. 7, 2019; 18 pages.
International Preliminary Report on Patentability of International Patent Application No. PCT/US2019/017274 issued on Oct. 15, 2020, 10 pages.
Office Action issued in U.S. Appl. No. 17/045,366 dated Apr. 26, 2022, 13 pages.
Exam Report under Section 18(3) issued in United Kingdom Patent Application No. GB2016858.9 dated Dec. 8, 2021, 7 pages.
International Preliminary Report on Patentability of International Patent Application No. PCT/US2018/034422 issued on Oct. 15, 2020, 12 pages.
International Preliminary Report on Patentability of International Patent Application No. PCT/US2018/034418 issued on Oct. 15, 2020, 10 pages.
Exam Report under Section 18(3) issued in United Kingdom Patent Application No. GB2016840.7 dated Jan. 21, 2022, 4 pages.
Exam Report under Section 18(3) issued in United Kingdom Patent Application No. GB2016845.6 dated Jan. 21, 2022, 4 pages.
Office Action issued in U.S. Appl. No. 17/045,313 dated Jul. 5, 2022, 22 pages.
Exam Report under Section 18(3) issued in United Kingdom Patent Application No. GB2016845.6 dated Jul. 19, 2022, 3 pages.
Preliminary Office Action issued in Brazilian patent application BR112020020435-8 on Sep. 13, 2022, 6 pages with English Translation.
Office Action issued in Brazil Patent Application No. BR112020020447-1 dated Jan. 5, 2023, 6 pages with English translation.
Notice of Allowance issued in U.S. Appl. No. 17/045,313 dated Jan. 27, 2023, 8 pages.
Office Action issued in Brazil Patent Application No. BR112020020447-1 dated May 11, 2023, 3 pages with English summary.
Office Action issued in U.S. Appl. No. 18/313,423 dated Apr. 2, 2024, 21 pages.
Office Action issued in Brazil Patent Application No. 1220230018109 dated May 6, 2024, 6 pages with English Translation.

* cited by examiner

METHODS, APPARATUS AND SYSTEMS FOR CREATING BISMUTH ALLOY PLUGS FOR ABANDONED WELLS

CROSS-REFERENCE TO RELATED APPLICATIONS

This application is a continuation of U.S. patent application Ser. No. 15/733,723 filed on Oct. 5, 2020, which is the U. S. National Phase of International Patent Application No. PCT/US2019/017274, filed Feb. 9, 2019, which claims priority to and the benefit of U.S. Provisional Application No. 62/652,015, filed on Jun. 28, 2011, and is a Continuation in part of International Patent Application PCT/US2018/034418 filed May 24, 2018, and is a Continuation in part of International Patent Application PCT/US2018/034422 filed May 24, 2018, the entirety of each of which are herein incorporated by reference.

TECHNICAL FIELD

The subject disclosure relates to methods, apparatus and systems for creating wellbore plugs for abandoned hydrocarbon wells.

BACKGROUND

Wells for the production of hydrocarbons such as oil are created by using a drill bit supported by a drill rig to drill a borehole into an earth formation. After the borehole is drilled, sections of steel pipe, also referred to as casings, having diameters slightly smaller than the diameter of the borehole are placed in the borehole. The casings are fixed in the borehole using cement which is pumped into an annulus between the casing and the formation. The cement not only provides structural integrity to the casings, but isolates zones in the earth formation from one another. After drilling and casing, the well is "completed" by making perforations in the casing through which the hydrocarbons can pass from the surrounding formation into production tubing. Various techniques may then be used to produce the hydrocarbons from the formation.

Over the course of time, when the production of a hydrocarbon well declines to the extent that it no longer profitably produces hydrocarbons, it is common to abandon the well. In abandoning the well, production tubing is removed, and a determination is made regarding the condition of the cement in the annulus. If the cement is not deemed to be in excellent condition, it is common practice to remove the casing and the annulus cement and to fill or plug the remaining borehole with cement in order to prevent interzonal and surface communication, and contamination, as environmental factors are important, particularly in offshore settings. The cost of removing the casing and the annulus cement can be significant, e.g., millions of U.S. dollars, particularly in offshore wellbores. One reason for the signficant cost is that removal of the casing and annulus cement is notoriously complicated and requires very heavy and expensive rig equipment for pulling the casing out of the wellbore.

The most common material used for plugging wells is Portland cement, which is placed in the well as a slurry that hardens in due time. A cement plug consists of a volume of cement that fills a certain length of casing or open hole to prevent vertical migration of fluids. Cement satisfies the essential criteria of an adequate plug; it is durable, has low permeability, and is inexpensive. Furthermore, it is easy to pump in place, has a reasonable setting time and is capable of tight bonding to the formation and well casing surface. It also has a sufficient mechanical strength under compression, although its tensile characteristics are its major weakness.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

According to one aspect, methods, apparatus and systems are provided that use bismuth alloy as a plug in a wellbore and seating the plug so that it sets with an excess pressure on the alloy over the borehole fluid pressure along a desired seal height distance. The desired seal height distance is generally either regulated or an established industry practice for a wellbore, and is typically from one to five meters in length.

In one embodiment, the bismuth alloy of the plug can be an alloy of bismuth and tin. For example, the bismuth alloy can contain 58% bismuth by weight and 42% tin by weight. Other metals or other materials can possibly be included as part of the bismuth alloy, if desired. The bismuth alloy containing both bismuth and tin forms a single phase and expands upon solidification and thus is effective for permanent plugs. The bismuth alloy containing both bismuth and tin can have a high compression and tensile strength that is comparable to cement. Moreover, for plugs of up to five meters in length, the bismuth alloy containing both bismuth and tin can be cost effective.

In another embodiment, the bismuth alloy of the plug can be an alloy of bismuth and silver. For example, the bismuth alloy can contain 97.5% bismuth by weight and 2.5% silver by weight. Other metals or other materials can possibly be included as part of the bismuth alloy, if desired. The bismuth alloy containing both bismuth and silver forms a single phase and expands upon solidification and thus is effective for permanent plugs. The bismuth alloy containing both bismuth and silver can have a high compression and tensile strength that is comparable to cement. The bismuth alloy containing both bismuth and silver is particularly corrosion resistance and thus can be used to plug wells filled with corrosive fluid (such as formation fluid having relatively low pH). Furthermore, the bismuth alloy containing both bismuth and silver can have a high melting point (such as at or near 263° C.) and thus is effective for high temperature environments when plugging deep offshore wellbores. For plugs of up five meters in length, the bismuth alloy containing both bismuth and silver can be cost effective.

In one embodiment, where the plug is to be set in a non-permeable portion of a formation (e.g., a shale layer), the formation-wellbore wall interface is first prepared by carving grooves into the wall that permit liquid to escape as the alloy sets. In embodiments, a non-permeable formation layer (or non-permeable portion of the formation or impermeable formation layer or portion) as described herein has a characteristic permeability below 1 µDarcy, while a permeable formation layer (or permeable portion of the formation) as described herein has a characteristic permeability above 0.1 mDarcy. Helical grooves may be carved, or vertical grooves connected by horizontal or angled grooves may be formed in the non-permeable portion of the formation utilizing a laser. A barrier or shot-catcher may then be installed just at or below the grooved area of the formation, and the bismuth alloy is then deployed with a thermite or other suitable reaction heater to below the top of the groove(s). The heater is then initiated with electrical input sufficient to raise the temperature above the melting point of the alloy. When the alloy cools, it expands and forces any borehole fluid away from the wall, pushing fluid up and out of the groove(s). In addition, by deploying sufficient quantities of bismuth alloy, a pressure difference is established along the desired seal height distance. By way of example, a pressure difference of 50 to 60 psi may be generated by having a plug of approximately five meters in height.

In another embodiment, where the plug is to be set in a porous (or permeable) layer of a formation (e.g., a sandstone), the location of a cap rock (non-permeable layer) for that permeable layer is found. A barrier or shot-catcher may then be installed at a location in the permeable layer and the bismuth alloy is deployed with a thermite or other suitable reaction heater. The heater is then initiated with electrical input sufficient to raise the temperature above the melting point of the alloy, and pressure is applied which forces the alloy into the permeable layer of the formation (e.g., into the pores or pore space of the permeable layer), thereby displacing any brine at the formation—borehole interface into the formation. When the alloy cools, it expands and sets both in the permeable layer (e.g., into the pores or pore space of the permeable layer) and in the borehole. Sufficient quantities of the bismuth alloy are deployed so that the plug extends up into the cap rock layer, and a pressure difference is established along the desired seal height distance.

In one embodiment, a tool is provided to deliver the bismuth alloy and to pressurize the bismuth alloy as it cures. The tool includes a packer that extends around a portion of the tool and engages the casing in the borehole, a fluid path including an inlet located above the packer, a pump, and a fluid outlet located below the packer, a bismuth alloy storage portion which may also store thermite or another suitable reaction heater and which is adapted to release the bismuth alloy and thermite into the target area of the borehole (e.g., an area spanning the permeable layer and cap rock), and a liquid alloy position monitor whose output is used to stop the pump from pumping. In some embodiments, the liquid alloy position monitor takes the form of electrodes extending from the bottom of the tool. In some embodiments, the electrodes are mounted on a retraction arm or on arms with a sacrificial tension joint that may be broken.

In one aspect, the plugs generated using the described methods have particular structures that prevent displacement under differential pressures. By way of example, the bismuth alloy plug that is formed in situ interfacing to a non-permeable (e.g., shale) formation layer includes a first solid cylinder portion with one or more ribs extending along the outer surface of this cylinder, and a second solid cylinder portion of smaller diameter than the first solid cylinder portion. In some embodiments, the first solid cylinder portion may taper at its top end toward the diameter of the second solid cylinder portion. In some embodiments, the one or more ribs are helical, while in other embodiments, the one or more ribs include some vertical ribs with some horizontal or angled ribs connecting the vertical ribs. The plug is typically at least five meters in length but less than half a meter in diameter. The ribs are typically less than one centimeter in both width and radial height.

Also, by way of example, the bismuth alloy plug that is formed in situ interfacing to a permeable formation layer includes a first solid cylinder portions along with branched alloy structures (a dendritic web portion) that extend from the outer surface of the first cylinder and follow the pores of the permeable formation layer, and a second solid cylinder portion of smaller diameter than the first cylinder portion. Again, the top portion of the first solid cylinder portion may taper in diameter towards the diameter of the second solid cylinder portion. The plug is typically at least five meters in length but less than half a meter in diameter. The dendritic web portion of the plug may extend one, two, or even a few centimeters away from the first cylindrical portion depending on the squeezing pressure applied and the desired penetration distance required for achieving the requisite strength for preventing displacement of the plug under a differential pressure.

In another aspect, a method for plugging a wellbore is provided that involves determining a measured depth in the wellbore corresponding to a portion (or layer(s)) of the formation that will interface to a plug when formed in situ. At least one property (such as pH of wellbore fluid, temperature, or pressure) at the measured depth in the wellbore is determined. The property(ies) at the measured depth in the wellbore can be used to select or rule out an alloy of bismuth and tin or an alloy of bismuth and silver for use in forming a plug in situ at the measured depth. The property(ies) at the measured depth in the wellbore can also be used to derive one or more additional parameters (such as a maximum allowed temperature based on pressure) to select or rule out an alloy of bismuth and tin or an alloy of bismuth and silver for use in forming a plug in situ at the measured depth.

Additional aspects, embodiments, objects and advantages of the disclosed methods may be understood with reference to the following detailed description taken in conjunction with the provided drawings.

DETAILED DESCRIPTION

Figure 1:
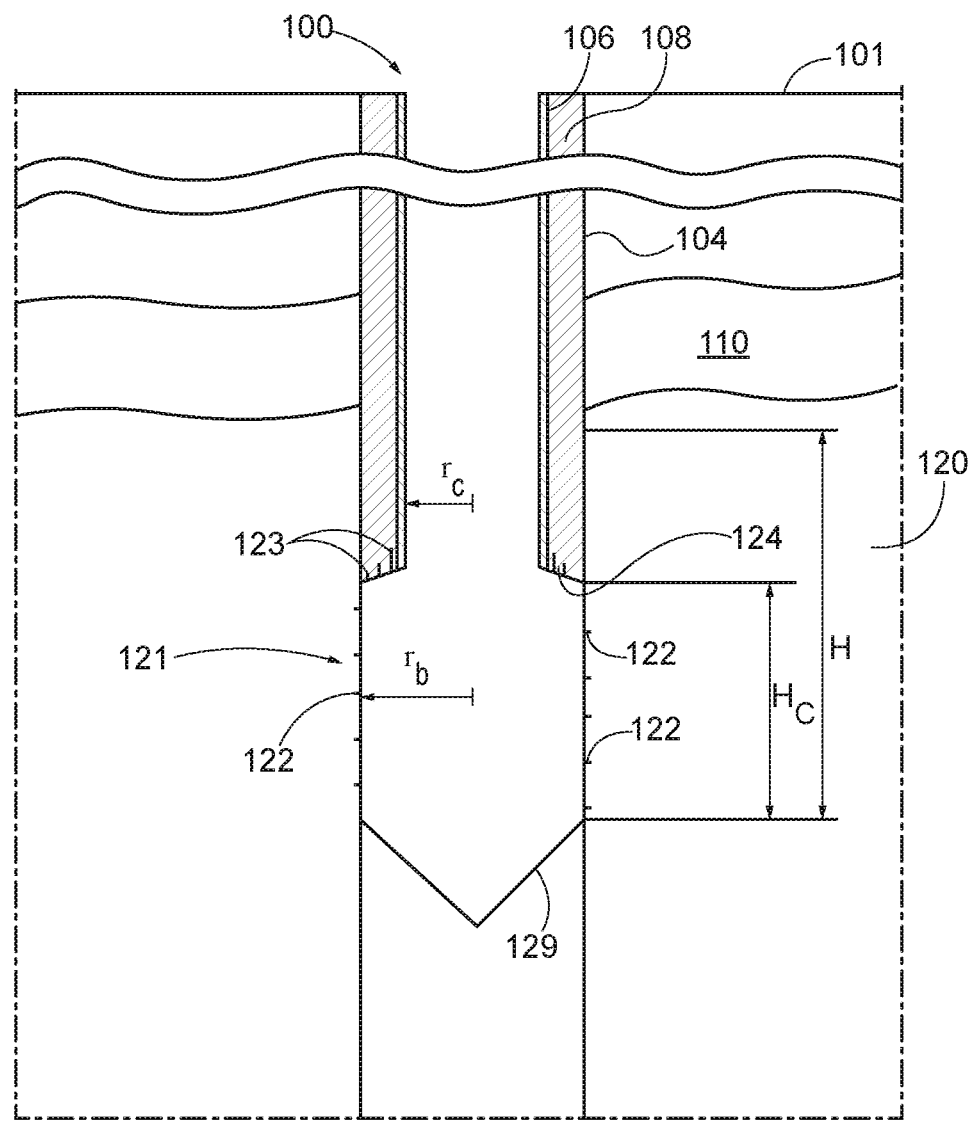
FIG. 1 is a diagram of a wellbore in a formation prepared for plugging at a non-permeable layer.

The present disclosure is directed to methods, apparatus and systems for using a bismuth alloy as a plug in a wellbore and seating the plug so that the plug sets with an excess pressure on the plug over the borehole fluid pressure along a desired seal height distance.

Generally, bismuth alloys may be considered for use in plug-and-abandonment wells, such as offshore wells. Alloy seals may be considerably shorter than cement plugs and may be set without rigs, thereby reducing well-abandonment costs. Bismuth alloys have various advantages over cement: the alloys expand in volume during confined solidification, thereby forming a fluid-tight seal; they are inert to downhole fluids; and their strength can withstand expected compressive and tensile loads without material failure. Solid bismuth alloys may be deposited into the borehole over a preinstalled barrier or shot-catcher. A thermite or other suitable reaction heater may be initiated with electrical input, sufficient to raise the temperature well above the melting point of the bismuth alloy. The thermite heater core tube may or may not be removed, and the expansion of the bismuth alloy during solidification may provide a seal.

In one embodiment, the bismuth alloy of the plug can be an alloy of bismuth and tin (BiSn alloy). For example, the bismuth alloy can be a eutectic mixture of bismuth (Bi) and tin (Sn) containing 58% bismuth (Bi) by weight and 42% tin (Sn) by weight and have a melting point of 138° C. and a density of 8.72 kg/L. Other metals or other materials can possibly be included as part of the bismuth alloy, if desired. The bismuth alloy containing both bismuth and tin forms a single phase and expands upon solidification and thus is effective for permanent plugs. The bismuth alloy containing both bismuth and tin can have a high compression and tensile strength that is comparable to cement. Moreover, for plugs of up five meters in length, the bismuth alloy containing both bismuth and tin can be cost effective.

In another embodiment, the bismuth alloy of the plug can be an alloy of bismuth and silver (BiAg alloy). For example, the bismuth alloy can be a eutectic mixture of bismuth (Bi) and silver (Ag) containing 97.5% bismuth (Bi) by weight and 2.5% silver (Ag) by weight and have a melting point of 263° C. and a density of 9.82 kg/L. Other metals or other materials can possibly be included as part of the bismuth alloy, if desired. The bismuth alloy containing both bismuth and silver forms a single phase and expands upon solidication and thus is effective for permanent plugs. The bismuth alloy containing both bismuth and silver can have a high compression and tensile strength that is comparable to cement. The bismuth alloy containing both bismuth and silver can be particularly corrosion resistance and thus can be used to plugs wells filled with corrosive fluid (such as formation fluid with relatively low pH). Furthermore, the bismuth alloy containing both bismuth and silver can have a high melting point (such as at or near 263° C.) and thus is effective for the high temperature environments when plugging deep offshore wellbores. Moreover, for plugs of up five meters in length, the bismuth alloy containing both bismuth and silver can be cost effective.

However, some bismuth alloys can be non-wetting, which can result in borehole fluid remaining between the alloy plug and the formation. More problematically, a chemical bond between the mineral rock surface and bismuth alloy does not form, and therefore a mechanical friction fit is relied upon. Thus, under certain differential pressure conditions, the bismuth alloy plug may undergo undesirable displacement. There is no guarantee that there is a pressure seal.

The methods, apparatus and systems of the present disclosure are directed towards two primary scenarios: a first scenario where the plug is to be set in a non-permeable layer of a formation; and a second scenario where the plug is to be set across both non-permeable and permeable layers of a formation.

According to one aspect, methods, apparatus and systems are provided for the plugging of an offshore wellbore. The methods, apparatus and systems are directed to wireline (WL), slickline, or coiled tubing applications which may be deployed, e.g., from an offshore production platform or from a ship (boat). For purposes herein, "wireline" is defined as a cabling technology used to lower equipment or measurement devices (also called "tools" or a "tool string") from a surface into oil and gas wells, where signals (data) may be transmitted via the cable from the equipment or measurement device to the surface. For purposes herein, "slickline" is defined as a non-electric cable, usually single-stranded, that is used to place, recover, or adjust wellbore equipment such as plugs, gauges and valves in oil and gas wells. Typically, slicklines do not transmit data. For purposes herein, "coiled tubing" is defined as a very long metal pipe which is supplied spooled on a large reel and used to carry out operations similar to wireline operations; i.e., to lower equipment or measurement devices (also called "bottom hole assemblies") at the bottom of the tubing from a surface into oil and gas wells. Slicklines, wirelines, and coiled tubing are raised and lowered in the well from a surface which may be a platform, a ship, or the formation itself and do not require the use of heavy rigs, such as might be required for removal of casing from a wellbore. Thus, according to one aspect, the methods, apparatus and systems for plugging an offshore wellbore may be directed to "rigless" methods, apparatus, and systems, where for purposes of this document, the terms "rigless" or "without a rig" are defined as methods, apparatus and systems that are equipped to intervene in a well, but not designed for or capable of pulling hundreds of meters of casing out of a wellbore without using a rig. A defining aspect of what is considered "rigless" or "without a rig" for purposes herein is the use of wireline or coiled tubing to relay an intervention tool into a well. A defining feature of a coiled tubing or wireline, i.e., as meant herein for defining a "rigless" intervention, is the storage of the wireline or coiled tubing by way of spooling around a drum or other cylindrical storage device. In contrast, a "rig" that is capable of pulling hundreds of meters of casing out of a hydrocarbon wellbore requires a structure such as a derrick, to sequentially add/remove long, heavy and rigid lengths of pipe, that are incapable of functionally being stored by being flexibly spooled around a drum or other cylindrical container.

Figure 3C:
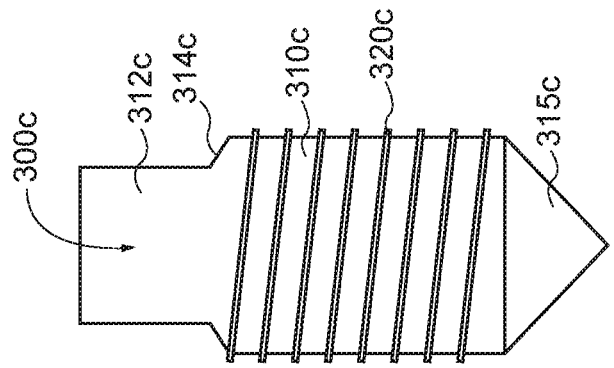
FIG. 3c is a diagram of a third solidified plug generated in a wellbore.
Figure 3B:
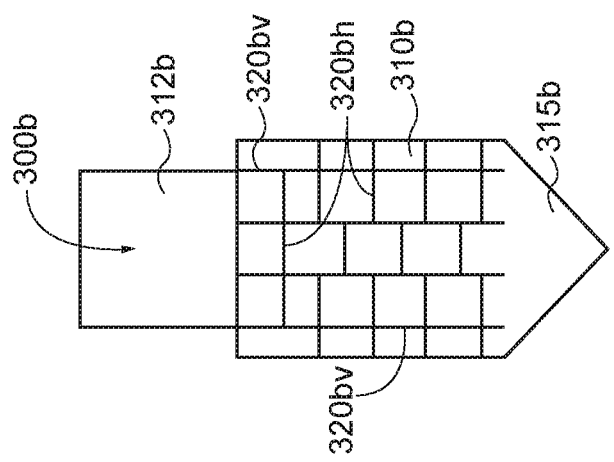
FIG. 3b is a diagram of a second solidified plug generated in a wellbore.
Figure 3A:
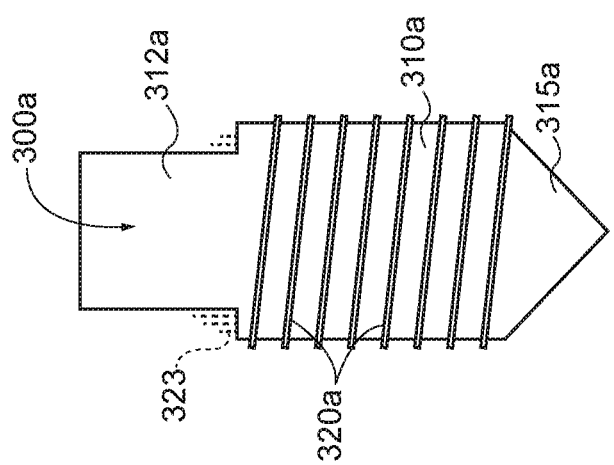
FIG. 3a is a diagram of a first solidified plug generated in a wellbore.

Turning to FIG. 1, an offshore abandoned wellbore 100 is seen extending downward from a sea floor 101 and having a wall 104, a casing 106 along a portion of the wall, and cement 108 therebetween. The wellbore 100 extends through a formation 110 having multiple layers. A non-permeable shale layer 120 is identified for receiving a plug A portion 121 of the shale layer 120, and is shown prepared with the casing and cement removed and with one or more notches or grooves 122 which are etched into the wellbore wall 104 with a laser tool (e.g., a tool such as disclosed in U.S. Pat. No. 8,627,901 to Underwood, et al., or in U.S. Pat. No. 8,701,794 to Zediker et al.). For purposes herein, the words "notch" and "groove" are used interchangeably and are to be broadly interpreted to include, but not be limited to a channel, trench, hollow, indentation, slot, and cleft. The one or more notches 122 are continuous along at least a portion of the wall where a first cylindrical portion of the plug is to be located. In one embodiment, the one or more notches are helical. In another embodiment, the one or more notches include vertical notches which are connected by notches having a horizontal component such as horizontal or angled notches. In one embodiment, in addition to the notches along the wellbore wall 104, one or more additional notches 123 (continuous to notches 122) in, e.g., a spiral form or in concentric circles connected by radial spokes are formed on a shoulder 124 between the cement and casing and the non-permeable rock. The spiral or concentric circular notch(es) is/are of increasing depth (height) with depth increasing towards the casing. In another embodiment, the shoulder 124 between the cement and casing and the non-permeable rock may be tapered. The tapered shoulder 124 may include or define the notch(es) 123. A shot-catcher (or umbrella) 129 is shown located in the borehole. Examples of plugs that may get generated as a result of the arrangement shown in FIG. 1 are seen in FIGS. 3a, 3b, 3c and discussed hereinafter.

Figure 2:
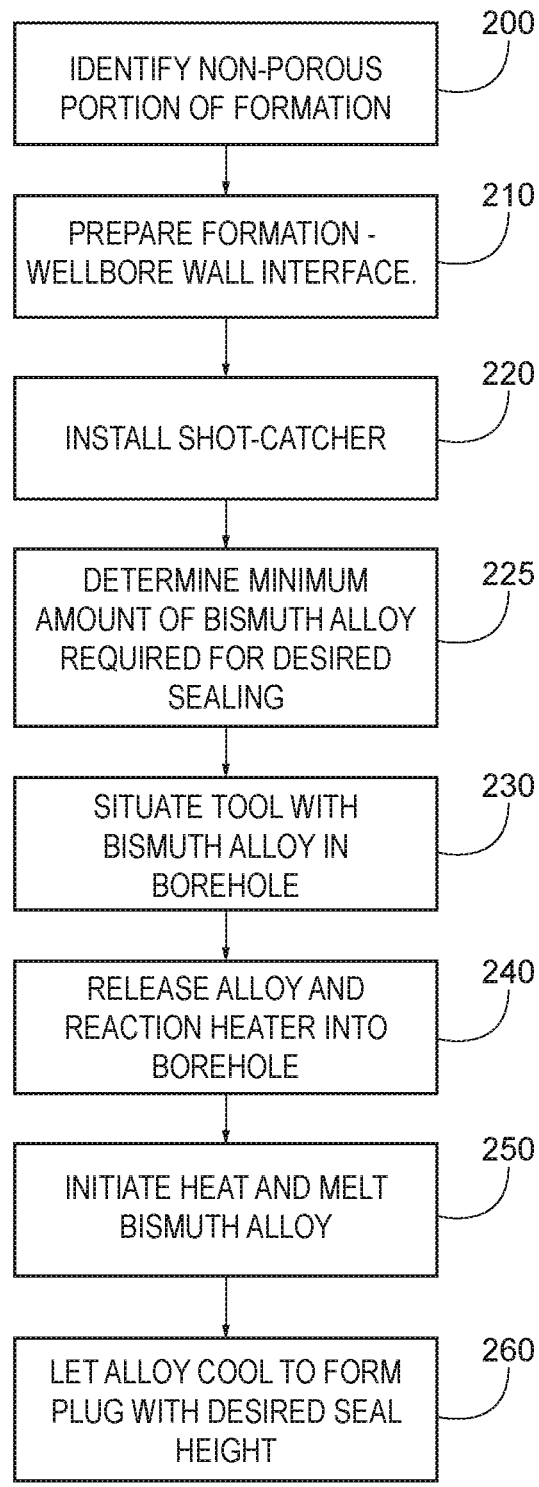
FIG. 2 is a flow chart of a method for plugging an abandoned wellbore at a non-permeable layer.

A method for plugging a wellbore is shown in FIG. 2. At 200, a non-permeable portion of a formation (e.g., a shale layer) is identified. The non-permeable shale layer 120 may be identified by review of logs of the well and/or formation previously generated in order to explore and/or exploit the formation. In one embodiment, the shale layer 120 that is identified is a relatively thick shale layer (e.g., tens of meters thick) that is closest to the surface of the formation (i.e., the seabed). At 210, the formation—wellbore wall interface is prepared by removing the casing and cement and carving one or more grooves into the wellbore wall for liquid escape as described hereinafter. More particularly, one or more helical grooves may be carved, or vertical grooves connected by horizontal or angled grooves may be generated utilizing, e.g., a laser. At 220, a barrier, umbrella or shot-catcher may then be opened out (i.e., deployed using a barrier deployment tool) just at or below the grooved area of the formation. At 225, a determination is made as to the minimum amount of bismuth alloy (e.g., bismuth-tin alloy or bismuth-silver alloy) required to obtain a desired sealing of the wellbore as discussed in more detail hereinafter. At 230, a tool containing at least the minimum amount of bismuth alloy and a thermite or other suitable reaction heater is situated in the borehole, e.g., using wireline, slickline or coiled tubing, and at 240, the bismuth alloy and thermite is released to fill the borehole from the barrier up to the top of the prepared area and into a section of the cased portion of the borehole. The heater is then initiated with an electrical input at 250 and is sufficient to raise the temperature above the melting point of the alloy, thereby melting the alloy. As the alloy cools at 260, due to a pressure difference and buoyancy, it forces any borehole fluid away from the wall, and pushes the fluid up and out of the groove(s). The alloy also expands as it solidifies, but as it is not necessarily confined, the pressure difference and buoyancy are useful. Any borehole fluid arriving at the shoulder is directed by the taper of the shoulder and/or by grooves in the shoulder to the cased section where it may float to the surface. By deploying at least the minimum quantity of bismuth alloy, a pressure difference between the resident borehole fluid and the alloy is established along the desired seal height distance of the resulting plug.

In order to generate a pressure difference along the seal distance, it will be appreciated that the bismuth alloy pressure must be greater than the pressure in the brine (borehole fluid) below the bismuth alloy. Since the formation at the location of the plug is non-permeable, any brine trapped at the wall of the borehole will not naturally be pushed out by the bismuth alloy expansion during solidification. Accordingly, the continuous grooves are provided, so that through buoyancy, an escape pathway for the brine is available. Continuous pathway enables pressure continuity of the connected brine, so that the gravity head of the alloy over the brine provides the needed pressure difference to remove the resident brine. Otherwise, any increase in the alloy pressure over the static pressure, i.e., $\Delta P_A$, will elevate both the alloy and the brine pressure. Therefore, the gravity head for the alloy is relied upon as being larger over a given height compared to the brine in order to buoyantly remove the brine.

In order to achieve a desired $\Delta P_A$, a melted alloy height H is required according to:

$$H \geq \frac{\Delta P_A}{(\rho_A - \rho_w)g} + H_m \quad (1)$$

where $\rho_A$ and $\rho_w$ are the densities of the bismuth alloy and borehole brine respectively, g is the acceleration due to gravity, and $H_m$ is the minimum seal height desired.

In one embodiment, in order to be conservative, an alloy height of $H_c$ is added, where He is the height of the area where the casing has been removed such that $$H = \frac{\Delta P_A}{(\rho_A - \rho_w)g} + H_m + H_c \quad (2)$$

By way of example, a pressure difference of approximately 50 psi may be generated by having a plug of approximately five meters in height.

The volumetric amount of bismuth alloy required to generate the desired plug height H (as determined by either equation (1) or equation (2)) is determined from $$V = \pi r_c^2 H + \pi (r_b^2 - r_c^2) H_c + V_C + V_R + V_u, \quad (3)$$

where $r_b$ is the radius of the prepared area (which may extend up to the borehole wall or beyond the borehole wall and into the formation) and is known, $r_c$ is the radius of the casing and is known, $V_C$ is the volume of the etched channel(s) and is known (and generally de minimis), $V_u$ is the volume in the umbrella and is known, and $V_R$ is the volume of the casing removed in the section above the cavity of radius $r_b$, (if any, and is generally de minimis in any event) and is known. For purposes herein, the volume V is said to "substantially equal" the first two terms of equation (3) plus $V_u$ as $V_C$ and $V_R$ are generally de minimis. If the prepared area has a tapered portion, the V should be adjusted accordingly to include the taper volume. Again, in one embodiment, that adjustment may be considered de minimis such that the volume V may still be said to "substantially equal" the first two terms of equation (3) plus $V_u$.

It is noted that the volume V may be calculated by hand or by or through the use of a processor.

With the bismuth alloy having been deployed into the wellbore, having been heated to make it liquid and then cooled so as to force out the brine, a solid plug is generated. One example of such a solidified plug generated in a wellbore is seen in FIG. 3a where plug 300a is shown having a first cylindrical body portion 310a, a second cylindrical body portion 312a of smaller diameter than the first cylindrical body portion, a first end 315a shaped by the shape of the shot-catcher (e.g., conical), and one or more threads 320a (only one shown) extending proud of and helically running along the cylindrical first body portion 310a to the top of the cylindrical first body portion 310a. A possible spiral thread 323 increasing in height from outside to inside is also shown in phantom.

Another example of a solidified plug that might be generated in the wellbore is seen in FIG. 3b. Plug 300b is shown having a cylindrical first body portion 310b, a cylindrical second body portion 312b having a smaller diameter than the first cylindrical body portion, a first end 315b shaped by the shape of the shot-catcher, a plurality of vertical ribs 320bv extending proud of and helically running along the cylindrical first body portion to the top of the cylindrical first body portion as well as a plurality of horizontal ribs 320bh connecting the vertical ribs. It will be appreciated that in some embodiments, instead of horizontal ribs, the plug might have angled (arced) ribs connecting the vertical ribs. In fact, combinations of one or more of helical, vertical, horizontal, and arced ribs may get generated depending upon the etching of the non-permeable formation layer provided that the etching generated one or more pathways for fluid to escape up and away from the formation wall as the bismuth alloy solidifies. The ribs or the spiral grooves also provide hindrance to displacement of the plug.

Yet a third example of a solidified plug that might be generated in the wellbore is seen in FIG. 3c. Plug 300c is shown having a first cylindrical body portion 310c, a second cylindrical body portion 312c of smaller diameter than the first cylindrical body portion, a tapered portion 314c at the top of the first cylindrical body portion 310c which tapers in diameter to the diameter of the second cylindrical body portion 312c, a first end 315c shaped by the shape of the shot-catcher (e.g., conical), and one or more threads 320c (only one shown) extending proud of and helically running along the cylindrical first body portion 310c to the top of the cylindrical first body portion 310c.

Figure 4:
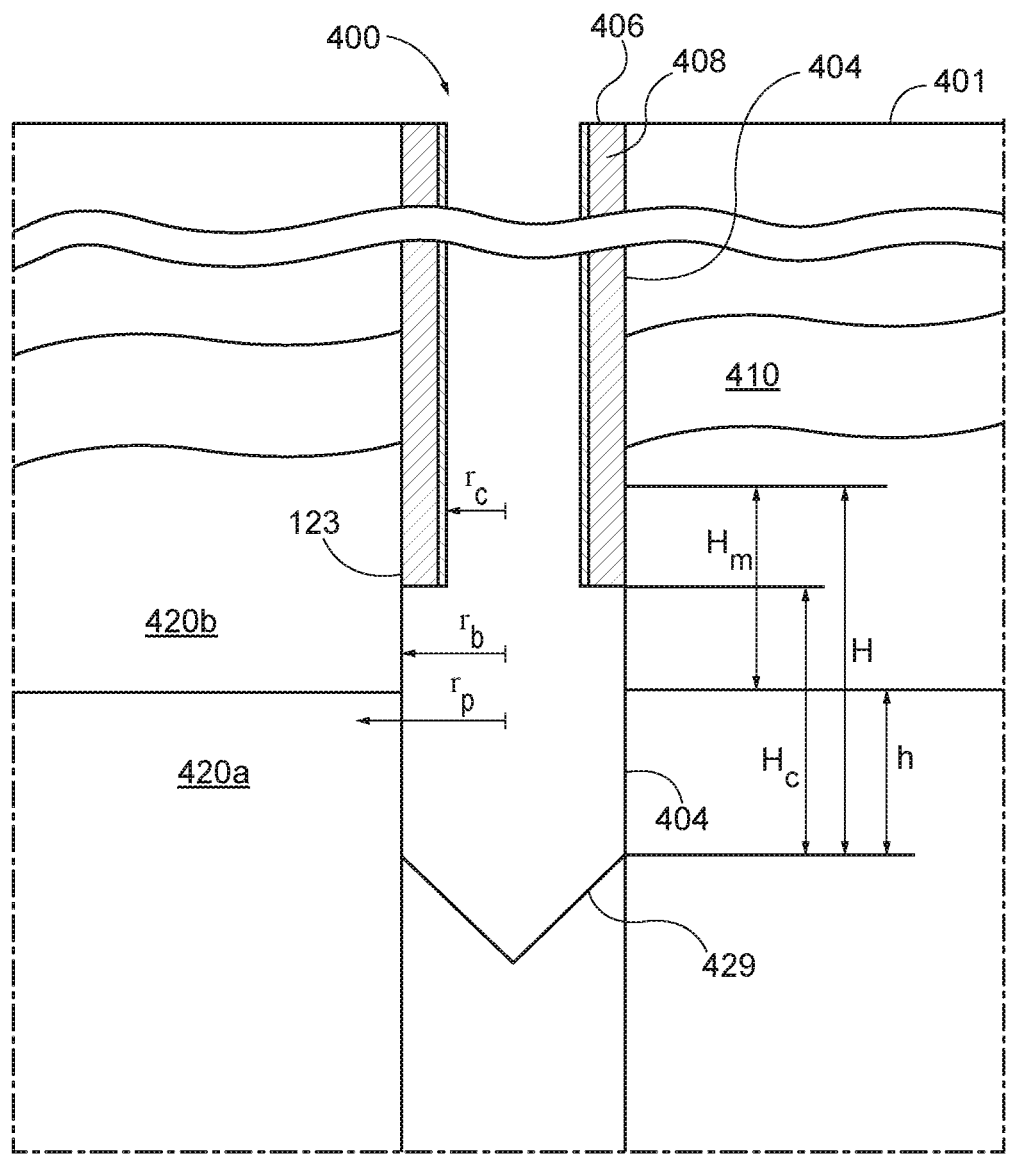
FIG. 4 is a diagram of a wellbore in a formation prepared for plugging at the interface of a permeable layer and a non-permeable layer.

While FIGS. 1, 2, and 3a-3c are directed to plugging a wellbore at a non-permeable layer of the formation, FIGS. 4, 5, 6a-6c and 7 are directed to plugging a wellbore at a permeable layer of the formation. As seen in FIG. 4, a wellbore 400 in a formation extends downward from a sea floor 401 and has a wall 404, a casing 406 along a portion of the wall, and cement 408 between the casing and the wall. The wellbore 400 extends through a formation 410 having multiple layers. A permeable layer (e.g., sandstone) 420a which is capped by a non-permeable layer 420b (e.g., shale) is identified for receiving a plug. The permeable layer 420a is shown prepared with the casing and cement removed adjacent to the interface of a permeable layer and the non-permeable cap layer. As a result, the diameter of the borehole at the non-permeable layer 420b where the casing 406 and cement 408 are located is shown as r c, while the diameter of the borehole at the permeable layer 420a and in the non-permeable layer where the casing and cement have been removed is shown as $r_b$. Again, $r_b$ is the radius of the prepared area which may extend up to the borehole wall (i.e., the cement-formation interface) or beyond the borehole wall and into the formation. The diameter to which the bismuth alloy penetrates the formation (as discussed hereinafter) is shown as $r_p$. The height of the permeable layer from the shotcatcher 429 to the non-permeable layer is shown as h, and the height of the area from which the casing and cement are removed in both the permeable layer and non-permeable layer is shown as $H_c$.

Figure 5:
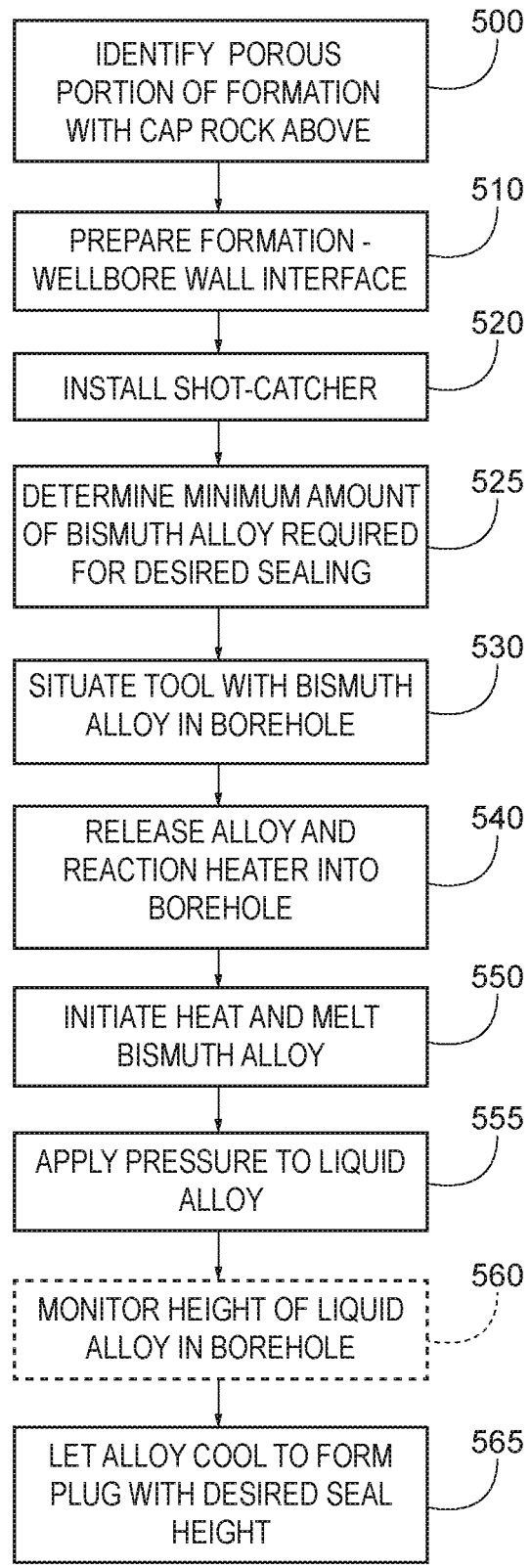
FIG. 5 is a flow chart of another method for plugging an abandoned wellbore at a permeable layer.

A method for plugging the wellbore 400 is shown in FIG. 5. At 500, a permeable (or porous) portion of a formation (e.g., a sandstone layer) having a non-permeable cap layer (e.g., a shale layer) is identified. The permeable portion of the formation having a non-permeable cap layer may be identified by review of logs of the well and/or formation previously generated in order to explore and/or exploit the formation. In one embodiment, the cap layer that is identified is a relatively thick shale layer (e.g., tens of meters thick) that is closest to the surface of the formation (i.e., the seabed). At 510, the formation—wellbore wall interface is prepared by removing the casing, cement, and possibly a part of the formation at the non-permeable layer. This section resembles a cavity within the wellbore. Optionally, the non-permeable cap layer wall (and shoulder) may also be etched with a laser or other device to form channels as previously described with reference to FIGS. 1 and 2. Also as previously described, optionally, the formation—wellbore interface may be prepared with a tapered shoulder. At 520, a barrier or shot-catcher may then be installed just at or below the prepared area of the formation. At 525, a determination is made as to the amount of bismuth alloy (e.g., bismuth-tin alloy or bismuth-silver alloy) required to obtain a desired sealing of the wellbore (as discussed in more detail hereinafter). At 530, a tool containing at least the required amount of bismuth alloy and a thermite or other suitable reaction heater is situated in the borehole, e.g., using wireline, slickline or coiled tubing, and at 540, the bismuth alloy and thermite is released to fill the borehole from the barrier upward. The heater is then initiated (with electrical input) at 550 and is sufficient to raise the temperature above the melting point of the alloy, thereby melting the alloy and at 555, pressure is applied as described hereinafter to the liquid alloy to force some of the alloy into the permeable layer, thereby pushing borehole liquid (brine) into the formation. Optionally, at 560 the height of the liquid alloy in the borehole and above the permeable layer is monitored in order to prevent too much movement of the alloy into the permeable layer with a concomitant decrease in plug height. The height of the liquid alloy may be used as feedback to control the pressure application. When the alloy cools at 565, it expands upon solidification and a pressure difference is established along the desired seal height distance.

According to one aspect, in selecting the amount of alloy to utilize, the following points are considered. After alloy pellets are delivered and melted, the height of the molten alloy should be more than the borehole height $H_m$ (the design specification for the minimum height requirement of the alloy over the shale interval) over which the alloy is intended to be set. The pressure that is applied at 555 may be applied in different manners. For example, the pressure may be applied through a water column above the molten alloy through the use of a surface pump so that the elevation in the bottom-hole pressure is nearly the same as the intended intrusion pressure. Alternatively, and as described hereinafter with respect to FIGS. 6a-6c, a packer may be set above the interval with an internal pump within the tool that pumps fluids from above the packer into the packed-off region.

Turning to the second alternative first, the borehole may be only partially filled with brine. This means that the formation pressure is less than the hydrostatic head in a filled borehole. With a schematic representation of the plug region as shown in FIG. 4, it should be understood that $r_b$, $H_m$, $V_C$ and h are fixed, where $V_C$ is the volume of the channels etched on the shale surface (if any), and $r_p$ is assumed. For this chosen geometry, the volume of alloy, $V_A$, that penetrates into the permeable layer can be calculated by $$\pi(r_p^2-r_b^2)\varphi h+\pi(r_p-r_b)(r_p^2-r_c^2\varphi=V_A \qquad (4)$$

where, $\varphi$ is the porosity, and as set forth above, h is the permeable bed height (into which alloy is to be pushed), $r_c$ is the casing radius, $r_b$ is the borehole radius, and $r_p$ is the penetration radius. It is noted that the volume from the equation is slightly larger than the volume of alloy penetrating the formation because an assumption is made that the cement behind the casing has the same penetration volume as the formation. This is usually an over-estimate. It is also noted that the height across the non-permeable layer does not contribute to the penetration volume of the alloy, except for what is present in the surface channels (if any).

At the bottom of the prepared portion of the formation, an umbrella may be set to prevent alloy from dropping below the prepared portion. If the volume within the umbrella container is $V_u$, the total alloy volume $V_{TA}$ other than the cylindrical portion of the plug may be calculated according to $$V_{TA} = V_A + V_C + V_u. \quad (5)$$

The minimum volume of the alloy in the rest of the borehole $V_a$ may be calculated by $$V_a = \pi r_b^2 (H_c - h) + \pi r_b^2 h + \pi r_c^2 (H - H_c) + V_R + V_T \quad (6)$$

where $H_c$ is the height of the area from which the casing and cement are removed in both the permeable layer and non-permeable layer (as previously described), $V_R$ is the casing volume removed above $H_c$ (if any), and $V_T$ is the volume of the tapered area (if any). Thus, the minimum required total alloy volume where the plug is being set partially in a permeable portion of the formation ($V_p$) is calculated as $V_p = V_{TA} + V_a$. It will be appreciated that $V_p$ may be calculated manually or through the use of a processor.

According to one aspect, after setting the bottom umbrella, and before dropping the bismuth alloy pellets, a good contact of the brine with the formation is maintained. A simple injection of water into the borehole may be used to increase the pressure in the borehole by $\Delta P_w$ resulting in an influx of water $q_w(t)$ into the permeable layer. For injection controlled from the surface, the volume added to the borehole in order to maintain the same pressure may be measured, and $q_w(t)$ may be inferred over a sufficiently long interval such that storage effects are not relevant. For an interval set with a packer, the pumping rate into the interval can be monitored in order to maintain the pressure increase. Alternatively, the pressure may be elevated by pumping liquid either at the surface or into the packed-off interval as the case may be. Knowing the compressibility of the pumped brine, and the decay rate of pressure after pumping is stopped, the flow rate may also be estimated, after ignoring log(t) dependence on pressure-drop versus flow rate dependence, i.e., the average flow rate over a specified time interval is sufficient. Now, in order to estimate the alloy flow rate, a zeroth-order approximation may be utilized $$q_A(t) = \frac{\mu_w \Delta P_A}{\mu_A \Delta P_w} q_w(t), \quad (7)$$

where $P_A$ is the pressure of the molten alloy during intrusion and $q_A$ is the alloy flow rate. The time for alloy to penetrate a distance $r_p$ is determined according to $$T = \frac{V_A}{q_A(t)}, \quad (8)$$

which may be set to a desired value by adjusting the pressure $P_A$.

It will be appreciated that there are complicating factors in attempting to control the bismuth alloy flow rate into the formation by adjusting pressure. For example, while the temperature in the borehole is elevated through the igniting of a chemical source, the resulting thermal profile should stay above the melting point of the alloy to a distance $r_p$ for the time T. But the alloy flow rate $q_A$ cannot be arbitrarily raised without limit simply by increasing $\Delta P_A$ without limit. Once the pressure limit is reached, T cannot be reduced any further and this defines $T_m$, a minimum time. From a design point, once $T_m$ becomes the limit, $r_p$ must be computed based on $q_A(t)$ obtained with the maximum $\Delta P_A$. If this $r_p$ is insufficient to achieve the necessary plug strength, then the height h must be adjusted to be larger to meet the requirements necessary to prevent dislodging of the plug.

According to one aspect, it may be desirable to use a downhole system (as described hereinafter) to build pressure on the molten alloy since the necessary column height required to reach $\Delta P_A$ may exceed the time for temperature at $r_p$ to stay above the melting point.

In the situation where the borehole is completely filled with brine, it will be appreciated that the formation pressure is greater than the borehole pressure. A further elevation in alloy pressure is required in order to have it enter the permeable rock. Unlike the previous case where the borehole was assumed to be only partially filled with brine, and given the lack of an air column, the bottom-hole pressure may be rapidly increased by pumping brine into the wellbore at the surface. Monitoring the pressure at the well-head for building up the requisite elevation in pressure in order to equal $\Delta P_A$ may be an acceptable solution, although a downhole wireline-conveyed pump could also be utilized and in one embodiment could be advantageous in being able to reduce the time required to achieve the necessary pressure elevation.

In some instances, a $\Delta P_A$ limit to prevent unlimited intrusion into the rock may not be known. In reality, intrusion will not be unlimited since the upper limit for $r_p$ is restricted by the temperature profile of the formation. In particular, beyond a certain radius, the formation temperature will stay below the alloy melting point, and penetration of the molten alloy significantly beyond that radius is unlikely. If this radial location becomes (unnecessarily) large, the cavity may not be completely filled with the bismuth alloy, and as a result, the plug height may become smaller (shorter) than the regulatory requirement or recommendation developed through historical practice of the art with cement plugs. Therefore, it may be desirable to limit the volume of intruded alloy, by setting an upper value for the net pumped volume of brine into the isolated section of the well-bore interval or into the borehole at the surface. For cases where a downhole pump with an isolated packed-off interval is deployed, this is easily implemented, and an upper limit on the pumped volume may be set. The expansion volume of the alloy upon solidification does not need to be accounted for since the net volume limit for pumping is calculated based on $V_A$, and is approximately equal to the pumped volume.

According to one aspect, the limit method described may have certain drawbacks due to volume expansion and contraction resulting from the heating and thermite reaction products. For example, upon melting, there is a volume reduction in alloy, which in turn will reduce pressure, but this is likely to be more than offset by the volumetric expansion of borehole brine due to increase in temperature. Therefore, pressure is likely to increase rather decrease. With migration into the formation, and temperature reduction due to heat loss, the pressure may drop below the intrusion $\Delta P_A$ and therefore continued pumping may be needed to maintain it. However, pumping should stop once the alloy level drops to $H_m$ (with some tolerance) across the non-permeable region since no further intrusion is desirable in the permeable region.

According to one embodiment, a simple level switch that monitors the liquid alloy position is sufficient to ensure a limit on intrusion volume. The level switch may be implemented using two point or ring or bar electrodes mounted on a sonde, the resistance across which is monitored, with the electrodes set just above the desired plug height. Upon a precipitous drop in conductance at this height (indicating that the alloy has dropped below that point), pumping may be stopped instantly. Any continued intrusion of alloy into the permeable layer will lead to a decrease in pressure. But back-flow of alloy into well-bore is not possible since water sitting above the permeable layer cannot easily imbibe into the non-permeable layer. Therefore, the system remains stable without further intrusion until solidification. The consequence is that the volume of the alloy being forced into the permeable layer is limited. In other words, by measuring conductance at a particular height in the borehole and controlling pumping based on a change in the conductance at that particular height, alloy intrusion distance may be directly controlled.

Figure 6A:
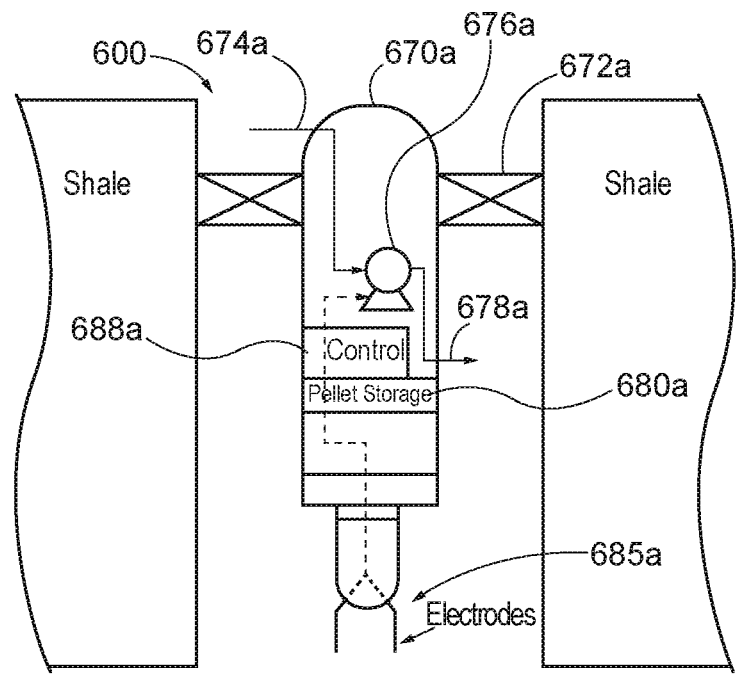
FIG. 6a is a diagram of a first tool assembly located in a wellbore and adapted for plugging the wellbore.

FIG. 6a is a diagram of a tool assembly located in a wellbore 600 and adapted for plugging the wellbore. The tool assembly 670a may include a packer 672a. The packer 672a is shown deployed and extending around a portion of the tool near the top of the tool and engaging the casing in the borehole. Also shown is a fluid path including an inlet 674a located above the packer 672a, a pump 676a, and a fluid outlet 678a located below the packer, a bismuth alloy storage chamber 680a which stores the bismuth alloy and may also store thermite or another suitable reaction heater and which is adapted to release the bismuth alloy and thermite into the target area of the wellbore 600, and an electrode assembly 685a which acts as a liquid alloy position monitor and is located at the bottom of the tool assembly. The tool 670a may also include a controller 688a coupled to both the electrode assembly 685a and the pump 676a. The controller 688a uses the output of the electrode assembly to control the pump 676a, i.e., to stop the pump when the electrode assembly indicates that the conductance being measured has dropped.

According to one aspect, since the alloy expands as it solidifies once pumping is stopped, there is a chance that the electrode assembly 685a, and hence the tool assembly 670a may be "frozen in" by the alloy. Thus, in one embodiment, the electrodes are mounted on a detachable mount that may be left behind. Alternatively, the electrodes may be protruding pin electrodes (as suggested by FIG. 6a) with a sacrificial tension joint that may be broken off. Replacement electrodes may be provided on the tool for later use in another borehole. As another alternative, the electrode assembly 685a may be provided with the necessary electronics to drive a finite current through the electrodes for measuring conductance. If the electrodes are detected to be frozen in by friction, the alloy directly around the electrodes may be melted through additional circuitry by resistive heating thereby permitting the tool with its electrodes to be pulled out.

Figure 6B:
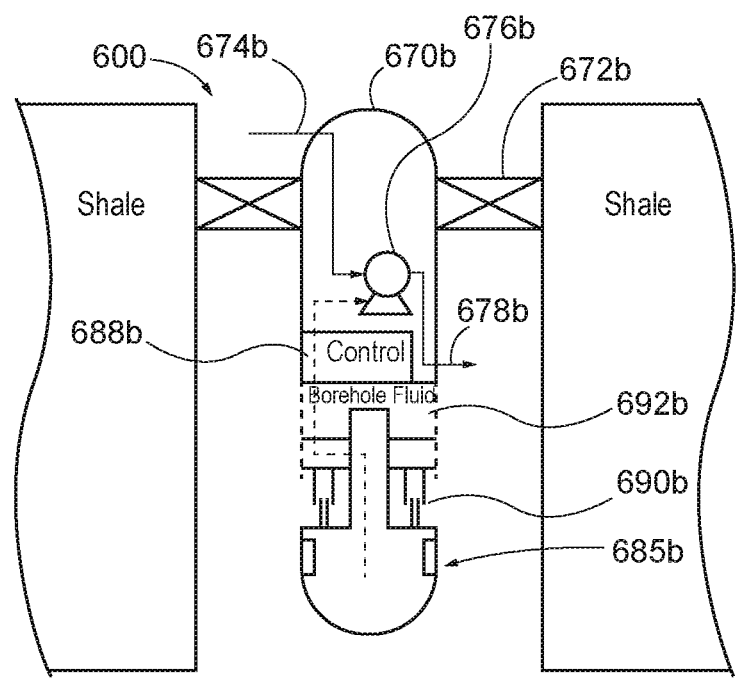
FIG. 6b is a diagram of a second tool assembly located in a wellbore and adapted for plugging the wellbore.

Another tool assembly adapted to plug a wellbore is seen in FIG. 6b. Tool assembly 670b is similar to tool assembly 670a in that it may include a packer 672b (shown deployed and extending around a portion of the tool near the top of the tool and engaging the casing in the borehole), a fluid path including an inlet 674b located above the packer 672b, a pump 676b, and a fluid outlet 678b located below the packer, a bismuth alloy storage chamber (not shown) which stores the bismuth alloy and may also store thermite or another suitable reaction heater and which is adapted to release the bismuth alloy and thermite into the target area of the wellbore 600, and an electrode assembly 685b which acts as a liquid alloy position monitor and is located at the bottom of the tool assembly. The tool 670b may also include a controller 688b coupled to both the electrode assembly 685b and the pump 676b. The controller 688b uses the output of the electrode assembly to control the pump 676b; i.e., to stop the pump when the electrode assembly indicates that the conductance being measured has dropped.

As seen in FIG. 6b, the electrode assembly 685b is provided with telescoping pistons 690b so that the electrode assembly may be retracted via linear actuation; i.e., pulled back toward the body of the tool. In order to avoid a resulting pressure variation, the tool assembly 600b is shown to include a fluid reservoir cavity 692b that has holes for pressure and fluid communication and which dispenses a volume of fluid into the borehole equal to the volume displacement of the retracted electrode assembly. Thus, no pressure change occurs within the isolated section of the borehole.

Figure 6C:
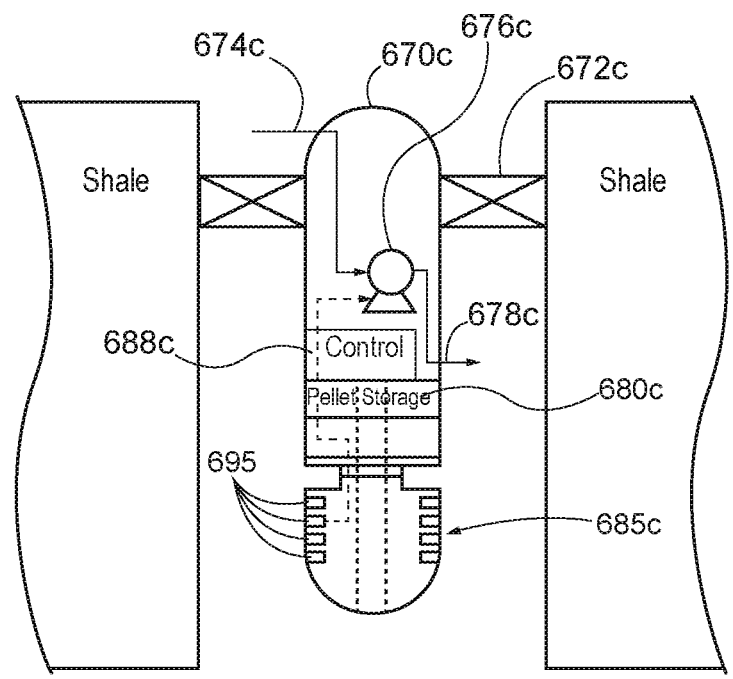
FIG. 6c is a diagram of a third tool assembly located in a wellbore and adapted for plugging the wellbore.

Another embodiment of a tool assembly for plugging a wellbore is seen in FIG. 6c. Tool assembly 670c is similar to tool assemblies 670a and 670b in that it may include a packer 672c (shown deployed and extending around a portion of the tool near the top of the tool and engaging the casing in the borehole), a fluid path including an inlet 674c located above the packer 672c, a pump 676c, and a fluid outlet 678c located below the packer, a bismuth alloy storage chamber 680c which stores the bismuth alloy and may also store thermite or another suitable reaction heater and which is adapted to release the bismuth alloy and thermite into the target area of the wellbore 600, and an electrode assembly 685c which acts as a liquid alloy position monitor and is located at the bottom of the tool assembly. The tool 670c may also include a controller 688c coupled to both the electrode assembly 685c and the pump 676c. The controller 688c uses the output of the electrode assembly to control the pump 676c; i.e., to stop the pump when the electrode assembly indicates that the conductance being measured has dropped.

As seen in FIG. 6c, the electrode assembly 685c includes a plurality of electrode pairs 695 which are adapted to detect conductance transition along the depth of the well and accordingly permit the controller 688c to ascertain the position of the alloy. The intrusion rate of alloy into the permeable layer then may be inferred from the rate of change of position and temperature in order to account for alloy expansivity. Based on this, an estimation may be made as to when the sonde bottom may be cleared of the alloy (including solidification), and the pump 676c may be stopped accordingly.

Figure 7:
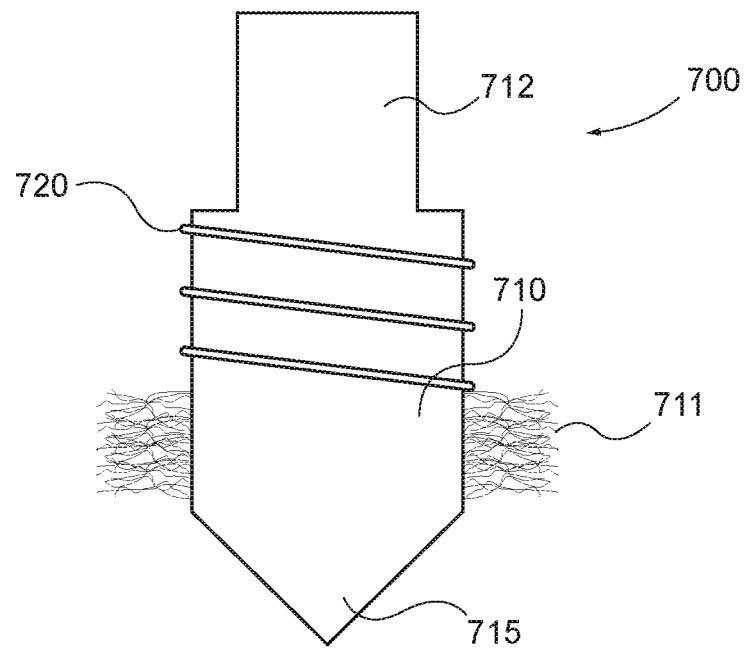
FIG. 7 is a diagram of a solidified plug generated in a wellbore located at the interface of a permeable layer and a non-permeable layer.

Using any of the tools of FIGS. 6a-6c, or any other tool permitting pressure to be applied to the bismuth alloy, and using the method of FIG. 5, a bismuth alloy plug is generated in the wellbore. FIG. 7 is a diagram of a solidified plug 700 generated in a wellbore located at the interface of a permeable layer and a non-permeable layer. Plug 700 is shown having a first cylindrical body portion 710, a dendritic web 711 (almost like a fuzzy beard) taking the form of the pores of the formation extending around the outer surface of a lower portion of the first solid cylinder portion, a second cylindrical body portion 712 of smaller diameter than the first cylindrical body portion extending above the first solid cylinder portion, a first end 715 shaped by the shape of the shot-catcher (e.g., conical) extending below the first cylindrical body portion. In some embodiments, where the non-permeable layer is etched before plug formation, the plug 700 may include one or more threads 720 extending proud of and running upwards along the top portion of the cylindrical first body portion. As with plugs 300a and 300b, these threads may be helical, and/or may include a combination of (i) vertical and (ii) horizontal or arced ribs. In addition, as previously described with respect to FIGS. 3a-3c, in some embodiments, the top portion of the first cylindrical body portion 710 may be tapered, and in some embodiments, a shoulder of the plug at the intersection of the first and second cylindrical body portions may have a spiral or concentric connected rings increasing in depth toward the middle of the plug.

Figure 8:
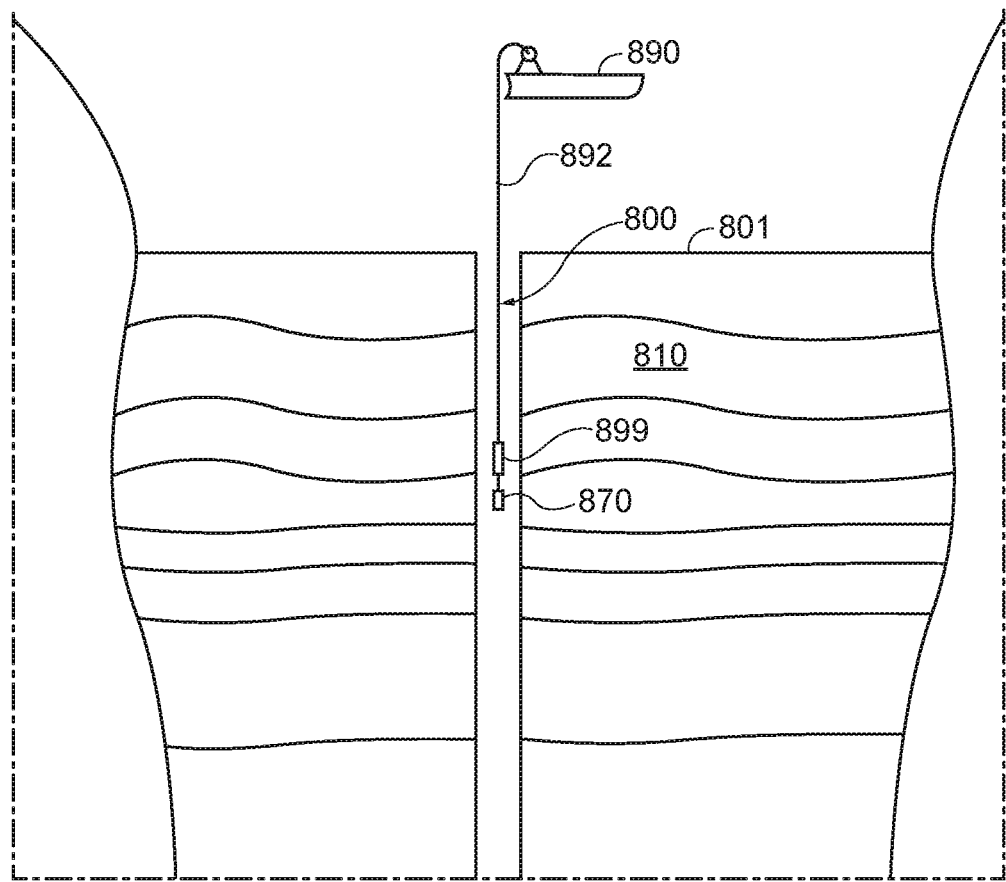
FIG. 8 is a schematic of a system for plugging an offshore well.

Turning now to FIG. 8, a schematic diagram is provided for a system for the rigless plugging an offshore wellbore 800. Wellbore 800 is seen traversing a formation 810 having a surface at seabed 801. A ship 890 is shown floating above the wellbore, and a cable or coil 892 (e.g., a wireline, slickline or coiled tube) is shown extending from the ship down into the wellbore 800. Extending from the cable or coil is a laser tool 899 as previously described which is used for preparing the wellbore—formation wall interface according to any of the previously described arrangements. In one embodiment, a tool string is provided with the laser tool 899 and a bismuth alloy plug generation tool assembly 870 such as previously described with respect to any of tools 670a, 670b and 670c. If desired, a separate barrier (umbrella) deployment tool (not shown) may be part of the string. Where the tool string is provided, the laser tool is located above the bismuth alloy plug generation tool so that the laser tool can prepare a portion of the wellbore, and then the tool string may be pulled upward to locate the umbrella or barrier just below the prepared area of the wellbore. and the bismuth alloy plug generation tool above the prepared area of the wellbore. Alternatively, the laser tool 899 may be run separately from the bismuth alloy plug generation tool assembly 870 (and barrier deployment tool), so that the laser tool 899 is first deployed from the ship to prepare the wellbore—formation wall interface. When the preparation is completed, the laser tool 899 is withdrawn, and the bismuth alloy plug generation tool assembly 870 is deployed.

Figure 9:
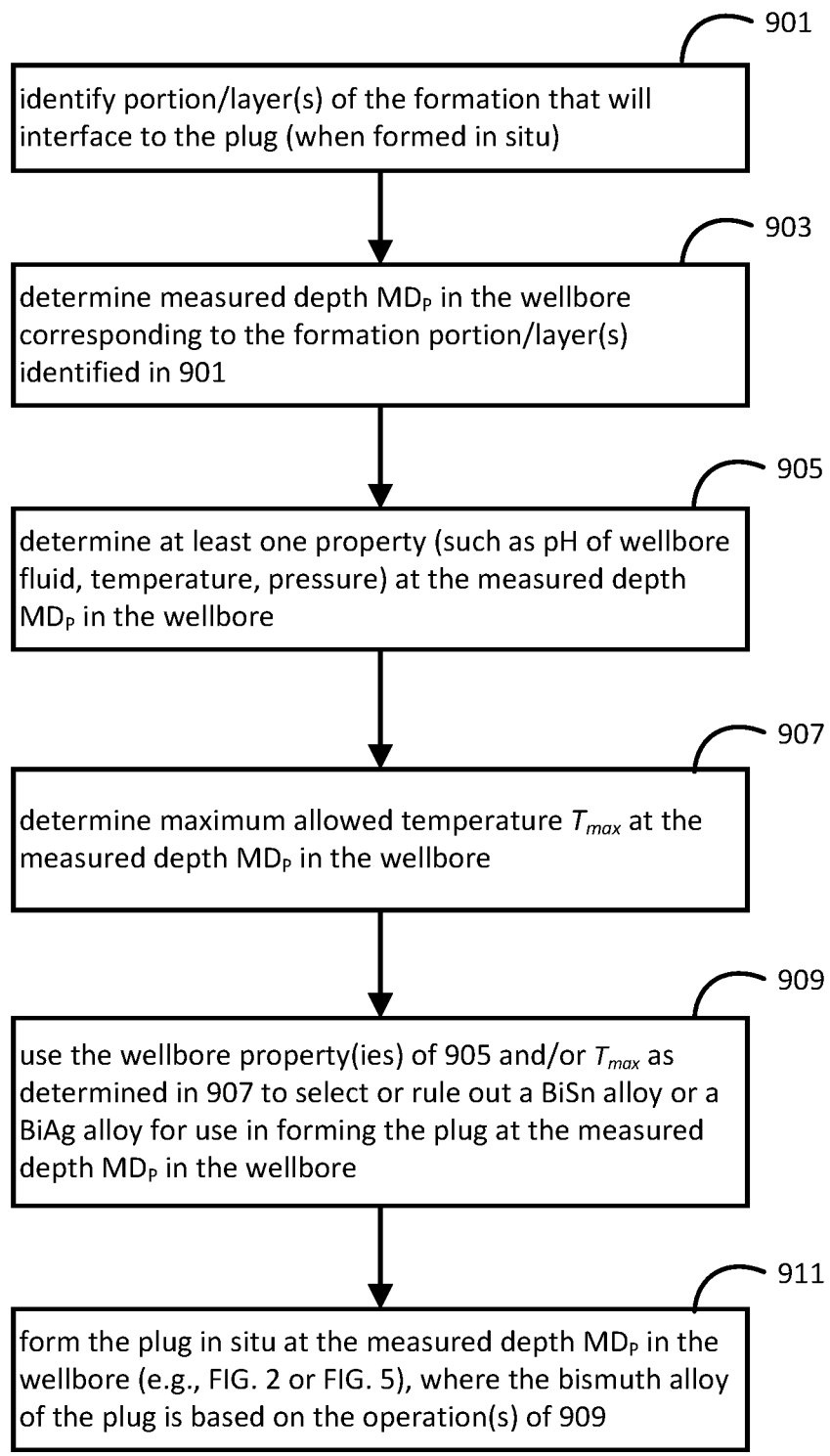
FIG. 9 is a flow chart of a method for selecting an alloy of bismuth and tin or an alloy of bismuth and silver for use in plugging a wellbore.

A method for selecting an alloy of bismuth and tin or an alloy of bismuth and silver for use in plugging a wellbore that traverses a formation is shown in FIG. 9. At 901, a portion (or layer(s)) of the formation that will interface to the plug (when formed in situ) is identified. Such formation portion (or layer(s)) may be identified by review of logs of the well and/or the formation previously generated in order to explore, drill the well and/or otherwise exploit the formation.

At 903, a measured depth $MD_P$ in the wellbore that corresponds to the formation portion (or layer(s)) identified in 901 is determined. The measured depth $MD_P$ may be determined by review of logs of the well and/or the formation previously generated in order to explore, drill the well and/or otherwise exploit the formation. The measured depth $MD_P$ can be represented by a value or range of values of measured depth corresponding to a length in the wellbore. Note that measured depth differs from true vertical depth in the wellbore in all but vertical wells.

At 905, at least one property at the measured depth $MD_P$ of the wellbore is determined. In embodiments, the at least one property can be one or more of the following properties: pH of wellbore fluid, temperature, pressure, or some other property for the measured depth $MD_P$. Such properties can be determined using a variety of sensing modalities. For example, at least one tool can be deployed (conveyed) and operated at or near the measured depth $MD_P$ in the wellbore to acquire one or more fluid samples of wellbore fluid at or near the measured depth $MD_P$, and the fluid sample(s) can be analyzed to measure pH, temperature and/or pressure of the wellbore fluid. The analysis can be carried out at the surface at the wellsite or at a remote laboratory, or possibly by a downhole fluid analysis module that is part of the tool. In another example, for pH sensing, one or more fluid samples of produced wellbore fluid that flows in or through the wellbore can be acquired and analyzed by a pH sensor to measure pH of the produced wellbore fluid, and the measured pH value can be equated to the pH value of the wellbore fluid at the measured depth $MD_P$. The fluid analysis and measurement of pH can be carried out at the surface at the wellsite or at a remote laboratory, or possibly downhole by downhole sensors disposed in the wellbore. Historical production log data that includes the pH value of the produced wellbore fluid over time can also be used to determine the pH of the wellbore fluid at the measured depth $MD_P$. The use of such historical production log data can be applicable in the event that the pH of the produced wellbore fluid is different from that of formation brine. The historical production log data can be obtained by equipment that samples wellbore fluid that flows in or through the wellbore and that analyzes the sampled wellbore fluid. The equipment that samples wellbore fluid that flows in or through the wellbore can be located at the surface (at the wellsite) or at a downhole location. The equipment that analyzes the sampled wellbore fluid can be located at the surface (at the wellsite or a remote laboratory) or at a downhole location. In yet another example, for temperature sensing, temperature at the measured depth $MD_P$ can be derived from historical well log data (such as open hole and cased hole historical production log data) and a geothermal gradient. The geothermal gradient can be a local geothermal gradient which is typically measured by determining the bottom open-hole temperature after drilling the wellbore. For the application of the geothermal gradient, a reference point corresponding to the measured depth $MD_P$ is needed. In many applications, the reference point can be a shallow depth of one or a few hundred meters. In yet another example, for pressure sensing, pressure at the measured depth $MD_P$ can be determined from historical production log data that includes measurements of pressure or from formation pressure as determined from exploration data or drilling data and depletion characteristics. Note that the original formation pressure can be considered an upper bound on the pressure at the measured depth $MD_P$ since injection of fluids to a degree exceeding the original formation pressure is not common.

At 907, a maximum allowed temperature $T_{max}$ at the measured depth $MD_P$ in the wellbore is determined. In embodiments, the value $T_{max}$ can be based on the boiling point of water at the pressure of the measured depth $MD_P$ as determined at 905. The value of $T_{max}$ is intended to avoid vaporization induced fracture of the formation portion/layer(s) at the measured depth. Specifically, the high melting point temperature required to liquify the bismuth alloy (particularly, the high melting point temperature of the alloy of bismuth and silver) can possibly cause the formation fluid to boil and lead to vaporization induced fracture of the formation portion/layer(s) and thus failure of the plug. The boiling point temperature of the formation fluid is dependent on the pressure in the wellbore and can be obtained through vapor pressure diagrams of water. The maximum allowed temperature can thus be tabulated as a function of pressure where the maximum allowed temperature for a given pressure is below the boiling point of water for the given pressure. In this case, the pressure at the measured depth $MD_P$ can be used as an input to the tabulated values of maximum allowed temperature as a function of pressure to determine the value of $T_{max}$ at the measured depth $MD_P$.

At 909, the wellbore property(ies) of 905 and/or $T_{max}$ as determined in 907 can be used to select (or rule out) an alloy of bismuth and tin or an alloy of bismuth and silver for use in forming the plug in situ at the measured depth $MD_P$.

For example, if the wellbore fluid pH as determined in 905 is less than a predetermined maximum pH level (e.g., 4) and thus indicates risk of corrosion to an alloy of bismuth and tin, then the alloy of bismuth and tin can be ruled out and the alloy of bismuth and silver can be selected unless another criterion indicates otherwise at 909.

In another example, if the wellbore fluid pH as determined in 905 is greater than a predetermined maximum pH level (e.g., 4) and thus indicates minimal risk of corrosion to the alloy of bismuth and tin and the temperature at the measured depth $MD_P$ as determined in 905 is less than a first predetermined temperature (e.g., 76° C.), then the alloy of bismuth and tin can be selected unless another criterion indicates otherwise at 909.

In yet another example, if the wellbore fluid pH as determined in 905 is greater than a predetermined maximum pH level (e.g., 4) and thus indicates minimal risk of corrosion to the alloy of bismuth and tin and the temperature at the measured depth $MD_P$ as determined in 905 is greater than a second predetermined temperature (e.g., 97° C.), then the alloy of bismuth and silver can be selected unless another criterion indicates otherwise at 909.

In still another example, if the wellbore fluid pH as determined in 905 is greater than a predetermined maximum pH level (e.g., 4) and thus indicates minimal risk of corrosion to the alloy of bismuth and tin and the temperature at the measured depth $MD_P$ as determined in 905 falls between the first and second predetermined temperatures (e.g., between 76° C. and 97° C.), then either one of the alloy of bismuth and tin or the alloy of bismuth and silver can be selected based on the required shear and tensile strength for the plug at 909.

In yet another example, if the value of $T_{max}$ as determined in 907 is not sufficiently less than the melting point of the alloy of bismuth and silver (e.g., 263° C.), then the alloy of bismuth and silver can be ruled out at 909.

At 911, the plug is formed in situ at the measured depth $MD_P$ in the wellbore, where the bismuth alloy of the plug is based on the operation(s) of 909. Thus, if the alloy of bismuth and tin is selected at 909, the alloy of bismuth and tin is used to form the plug in situ at 911. If the alloy of bismuth and silver is selected at 909, the alloy of bismuth and silver is used to form the plug in situ at 911. Any of the methods and systems described herein (such as the method FIG. 2 or FIG. 5) can be used to form the plug in situ at 911. Note that if both the alloy of bismuth and tin and the alloy of bismuth and silver are ruled out at 909, the plug can be formed from some other suitable material as deemed appropriate at 911.

Some of the methods and processes described above can be performed by a processor. The term "processor" should not be construed to limit the embodiments disclosed herein to any particular device type or system. The processor may include a computer system. The computer system may also include a computer processor (e.g., a microprocessor, microcontroller, digital signal processor, or general purpose computer) for executing any of the methods and processes described above.

The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

Some of the methods and processes described above can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

Although several example embodiments have been described in detail above, those skilled in the art will readily appreciate that many modifications are possible in the example embodiments without materially departing from the scope of this disclosure. Accordingly, all such modifications are intended to be included within the scope of this disclosure.

What is claimed is:

1. A method for plugging a wellbore having a casing and cement surrounding the casing and traversing a formation, comprising:
   a) determining a measured depth in the wellbore corresponding to a portion of the formation that will interface to a plug when formed in situ;
   b) determining at least one property of the wellbore at the measured depth in the wellbore; and
   c) using the at least one property of the wellbore as determined in b) to select or rule out an alloy of bismuth and tin or an alloy of bismuth and silver for use in forming a plug in situ at the measured depth; and
   d) determining at least one additional parameter based on the at least one property of b), wherein the at least one additional parameter is used in c) to select or rule out the alloy of bismuth and tin or the alloy of bismuth and silver for use in forming the plug in situ at the measured depth, wherein the at least one additional parameter comprises a maximum allowed temperature at the measured depth in the wellbore, where the maximum allowed temperature is based on a boiling point of water at the pressure for the measured depth.

2. The method according to claim 1, wherein:
   in c), the alloy of bismuth and silver is selectively ruled out for use in forming the plug in situ at the measured depth based on differences between the maximum allowed temperature and a melting point of the alloy of bismuth and silver.

3. A method for plugging a wellbore having a casing and cement surrounding the casing and traversing a formation, comprising:
   a) determining a measured depth in the wellbore corresponding to a portion of the formation that will interface to a plug when formed in situ;
   b) determining at least one property of the wellbore at the measured depth in the wellbore, wherein the at least one property of b) comprises at least one property selected from the following: pH of wellbore fluid, temperature and pressure at the measured depth in the wellbore; and
   c) using the at least one property of the wellbore as determined in b) to select or rule out an alloy of bismuth and tin or an alloy of bismuth and silver for use in forming a plug in situ at the measured depth, wherein in c), if the pH of the wellbore fluid at the measured depth is less than a predetermined maximum pH value that is indicative of risk of corrosion to the alloy of bismuth and tin, then the alloy of bismuth and tin is ruled out and the alloy of bismuth and silver is selected for use in forming the plug in situ at the measured depth unless another criterion indicates otherwise.

4. The method according to claim 3, further comprising:
   d) forming a plug in situ at the measured depth, where the plug is formed of the alloy selected in c).

5. The method according to claim 3, wherein:
the at least one property of b) is determined by equipment that samples wellbore fluid that flows in or through the wellbore and that analyzes the sampled wellbore fluid; or
the at least one property of b) is determined from historical production log data obtained by equipment that samples wellbore fluid that flows in or through the wellbore and that analyzes the sampled wellbore fluid.

6. The method according to claim 5, wherein:
the equipment that samples wellbore fluid is located at the surface or at a downhole location in the wellbore; and
the equipment that analyzes the sampled wellbore fluid is located at the surface or at a downhole location in the wellbore.

7. The method according to claim 3, wherein:
in c), the alloy of bismuth and tin is selected or ruled out for use in forming the plug in situ at the measured depth based on at least one of the pH of the wellbore fluid, the temperature and the pressure at the measured depth in the wellbore.

8. The method according to claim 3, wherein:
in c), the alloy of bismuth and silver is selected or ruled out for use in forming the plug in situ at the measured depth based on at least one of the pH of the wellbore fluid, the temperature and the pressure at the measured depth in the wellbore.

9. The method according to claim 3, wherein:
in c), if the pH of the wellbore fluid at the measured depth is more than a predetermined maximum pH value that is indicative of minimal risk of corrosion to the alloy of bismuth and tin and the temperature at the measured depth is less than a predetermined first temperature value, then the alloy of bismuth and tin is selected for use in forming the plug in situ at the measured depth unless another criterion indicates otherwise;
in c), if the pH of the wellbore fluid at the measured depth is more than a predetermined maximum pH value that is indicative of minimal risk of corrosion to the alloy of bismuth and tin and the temperature at the measured depth is greater than a predetermined second temperature value which is greater than the predetermined first temperature value, then the alloy of bismuth and silver is selected for use in forming the plug in situ at the measured depth unless another criterion indicates otherwise; and
in c), if the pH of the wellbore fluid at the measured depth is more than a predetermined maximum pH value that is indicative of minimal risk of corrosion to the alloy of bismuth and tin and the temperature at the measured depth falls between the predetermined first temperature value and the predetermined second temperature value, then one of the alloy of bismuth and tin and the alloy of bismuth and silver is selected for use in forming the plug in situ at the measured depth based on required shear and tensile strength for the plug.

* * * * *